(12) United States Patent
Fukui et al.

(10) Patent No.: US 7,754,695 B2
(45) Date of Patent: Jul. 13, 2010

(54) LIPASE INHIBITORS

(75) Inventors: Yuko Fukui, Takatsuki (JP); Masaaki Nakai, Minoo (JP); Sumio Asami, Ibaraki (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 12/285,144

(22) Filed: Sep. 30, 2008

(65) Prior Publication Data

US 2009/0042812 A1 Feb. 12, 2009

Related U.S. Application Data

(63) Continuation of application No. 11/660,784, filed as application No. PCT/JP2005/015212 on Aug. 22, 2005, now abandoned.

(30) Foreign Application Priority Data

Aug. 23, 2004 (JP) .............................. 2004-242666

(51) Int. Cl.
*A61K 31/70* (2006.01)
*A01N 43/04* (2006.01)

(52) U.S. Cl. .............................. 514/25; 514/26; 514/35

(58) Field of Classification Search .................. None
See application file for complete search history.

(56) References Cited

FOREIGN PATENT DOCUMENTS

| JP | 60-11912 | 3/1985 |
|---|---|---|
| JP | 01-102022 | 4/1989 |
| JP | 03-219872 | 9/1991 |
| JP | 03-228664 | 10/1991 |
| JP | 07-061927 | 3/1995 |
| JP | 08-259557 | 10/1996 |
| JP | 09-040689 | 2/1997 |
| JP | 09-291039 | 11/1997 |
| JP | 2002-275077 | 9/2002 |
| JP | 2004-510688 | 4/2004 |
| JP | 2005-137210 | 6/2005 |
| WO | 01/36436 A1 | 5/2001 |
| WO | 2005/000330 A1 | 1/2005 |

OTHER PUBLICATIONS

Cantos et al. J. Agric. Food Chem. (2003), vol. 51, pp. 6248-6255.*
Bacon et al., "Binding Affinity of Hydrolyzable Tannins to Parotid Saliva and to Proline-Rich Proteins Derived from It," J. Agric. Food Chem., 2000, vol. 48, pp. 838-843.
Nakai et al., "Inhibitory Effects of Oolong Tea Polyphenols on Pancreatic Lipase in Vitro", J. Agric. Food Chem., (2005), vol. 53, pp. 4593-4598.
Juhel et al., "Green Tea Extract (AR25®) Inhibits Lipolysis of Triglycerides in Gastric and Duodenal Medium In Vitro", J. Nutr. Biochem., (2000), vol. 11, pp. 45-51.
Moreno et al., "Inhibitory Effects of Grape Seed Extract on Lipases", Nutrition, (2003), vol. 19, pp. 876-879.
Yoshikawa et al., "*Salacia reticulata* and Its Polyphenolic Constituents with Lipase Inhibitory and Lipolytic Activities Have Mild Anti-obesity Effects in Rats", Amer. Soc. for Nutritional Sciences, (2002), vol. 132, pp. 1819-1824.
Han et al., "Anti-obesity Action of Oolong Tea", International Journal of Obesity, (Jan. 1999), vol. 23, No. 1, pp. 98-105.
Iwata et al., Effect of Oolong Tea on Plasma Lipids and Lipoprotein Lipase Activity in Young Women, Journal of the Japanese Society of Nutrition and Food Science, (1991) vol. 44, No. 4, pp. 451-259. (w/English-language translation).
Chen et al., "Clinical Efficacy of Oolong Tea on Anti-Simple Obesity", Journal of the Japanese Society of Nutrition and Food Science, (1998), vol. 20. No. 1, pp. 83-90 (w/English-language translation).
Hashimoto et al., Evaluation of the Anti-oxidative Effect (in vitro) of Tea Polyphenols, Biosci. Biotechnol. Biochem., (2003) vol. 67, No. 2, pp. 396-401.
International Search Report dated Nov. 22, 2005 issued in PCT/JP2005/015212 filed Aug. 22, 2005.

* cited by examiner

*Primary Examiner*—Patrick T Lewis
(74) *Attorney, Agent, or Firm*—Drinker Biddle & Reath LLP

(57) ABSTRACT

The present invention provides lipase inhibitory agents comprising a gallotannin or ellagitannin component(s) isolated from teas or *Tellima grandiflora* as well as foods and beverages and medicines containing said inhibitory agents.

The present invention provides lipase inhibitory agents comprising at least one of compounds represented by formula I below:

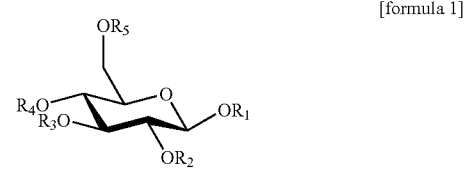

[formula 1]

wherein $R_1$, $R_2$ and $R_3$ independently represent H or a gallic acid residue, and $R_4$ and $R_5$ represent H or a gallic acid residue, or $R_4$ and $R_5$ together form an HHDP group represented by the formula below:

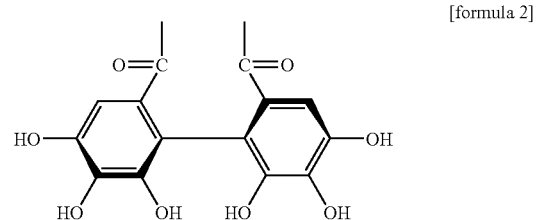

[formula 2]

provided that at least two of $R_1$ to $R_5$ represent a gallic acid residue or when all of $R_1$, $R_2$ and $R_3$ are H, $R_4$ and $R_5$ together form the HHDP group; as well as foods and beverages and medicines containing said lipase inhibitory agents.

16 Claims, 1 Drawing Sheet

[Figure 1]
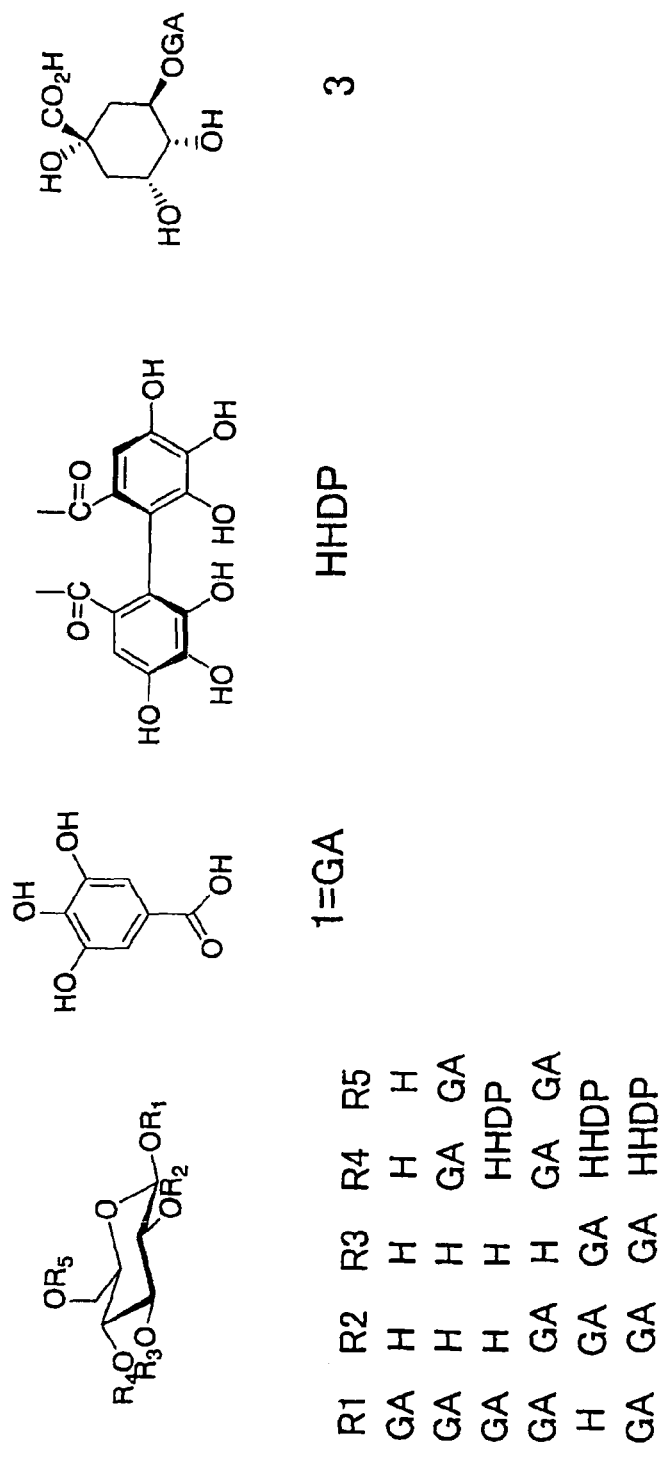

LIPASE INHIBITORS

This application is a continuation application of application Ser. No. 11/660,784, filed on Feb. 22, 2007, now abandoned which is a U.S. National Stage of International PCT Application No. PCT/JP05/15212, filed Aug. 22, 2005, which claims benefit of priority under 35 U.S.C. §119(a) to JP 2004-242666, filed Aug. 23, 2004, the disclosures of each are herein incorporated by reference in their entirety for all purposes.

TECHNICAL FIELD

This invention provides lipase activity inhibitory agents comprising a gallotannin or ellagitannin component(s) isolated from tealeaves or *Tellima grandiflora*.

BACKGROUND ART

With the recent tendency toward westernized eating habits in Japan, intake of high fat diet continues to increase. According to a National Nutrition Survey in Japan (1999), among people over 60, it is reported that although their energy intake is decreasing every year, their fat energy ratio exceeds the reasonable proportion of 25%, and 50 to 60% of those people are recognized to have high triglyceride and cholesterol values [Summary of 1999 National Nutrition Survey in Japan by The Ministry of Health, Labor and Welfare, Rinsho Eiyo (Clinical nutrition) 2001; 98(5): 577-588].

Obesity is one of the most severe diseases in present day society, caused by excessive fat intake. Excessive fat intake causes not only obesity, but also contracting disorders such as diabetes, hyperlipidemia, hypertension and arteriosclerosis. In Japan, Mazindole (registered trademark), an anorectic drug, is only one therapeutic drug with official approval for treating obesity. However, this drug is reported to have side effects such as excessive thirst (mouth dryness), constipation, epigastric distress, nausea and vomiting [Rinsyo Hyouka (Clinical evaluation), 1985; 13(2): 419-459, Clinical evaluation, 1985; 13(2): 461-515]. Overseas, Xenical (registered trademark) as a lipase inhibitor which suppresses fat absorption in the gastrointestinal tract, is on market as an obesity treatment drug. However, this drug is also reported to have side effects such as fatty stool, increased stool frequency, soft stool, diarrhea and stomachache. Therefore, using this drug is sometimes accompanied by concerns about safety (Lancet 1998; 352:67-172)

To prevent obesity, it is advantageous to reduce the caloric intake by controlling diet. However, it requires careful guidance on nutrition, making it difficult to practice in daily life. Therefore, inhibiting absorption of dietary lipids in the body in a safe and healthy manner is practical and useful for treatment of obesity and related diseases and in promoting health.

With these facts in mind, the development of "food for specified health uses" which is safe to use and is proven to be effective in treating humans is attracting a lot of attention. Food materials which inhibit increase of serum triglycerides after a meal, such as: a globin protein decomposition product that suppresses fat absorption by pancreatic lipase inhibitory activity [J. Nutr. 1988; 128: 56-60, Nihon Eiyou Shokuryou Gakkai-shi (Journal of Japanese society of Nutrition and Food Science) 1999; 52(2): 71-77, Kenkou Eiyou Shokuhin Kenkyu (Health food and nutrition food Research) 2002; 5(3): 131-144]; diacylglycerol with different digestion and absorption features compared to triacylglycerol (J. Am. Coll. Nutr. 2000; 19(6): 789-796, Clin. Chim. Acta. 2001; 11(2): 109-117); eicosapentaenoic acid (EPA) and docosahexanoic acid (DHA) purified from fish oil; are on market as foods for specified health use until now.

Lipase inhibitors derived from plants are also attracting attention in recent years. Especially, as to the polyphenols with lipase inhibitory activity, for example: tannin from bark (JP Shou 60-11912-B); tannins, flavonoids and glucosides thereof from leguminous plant (Cassia mimosoides L.var..nomame Makino) (JP Hei 8-259557-A); epigallocatechin gallate which is the main component in green tea, and lipid-absorption-suppressing food containing the epigallocatechin gallate (JP Hei 3-228664-A); lipase inhibitory agent containing water extracts from green pepper, shimeji mushrooms, pumpkin, *Grifola frondosa* (maitake), Hizikia fusiforme, green tea, oolong tea, and others (JP Hei 3-219872-A); flavons and flavonols (JP Hei 7-61927-A); hydroxybenzoic acids (gallic acid) (JP Hei 1-102022-A); triterpenes and derivatives thereof (JP Hei 9-40689-A); and anti-obesity medicine containing procyanidin from Tamarind as an active ingredient (JP Hei 9-291039-A) are reported. Also, the lipase inhibitory effect of grape seed extract (Nutrition 2003; vol. 19, (10), 876-879), the lipase inhibitory effect and anti-obesity effect of polyphenol from Salacia exhibited in rats (J. Nutr. 2002, 132, 1819-1824), the anti-obesity effect of oolong tea extract exhibited in rats (Int. J. Obes. 1999, 23 98-105), and others are known.

However, reported lipase inhibitory agents from the plants mentioned above are not sufficiently effective. For instance, since they originate from natural sources, there is a problem in maintaining stable lipase inhibitory activity when the content of the active ingredient in the plant is not clearly known. Moreover, use of an inhibitory agent derived from plants with less preference will raise a flavor problem when used in foods and/or beverages. For example, reports on lipid-improving effect of oolong tea are: significant decrease in blood triglyceride levels after drinking 1330 ml/day of commercial oolong tea for 6 weeks [Nihon Eiyou Shokuryou Gakkai-shi (Journal of Japanese society of Nutrition and food science.) 1991; 44(4): 251-259]; and oral administration of oolong tea (2 g×4/day) for 6 consecutive weeks to 102 males and females with simple obesity resulted in more than 1 kg weight loss in 67% of the subjects and significant improvement in the subjects with high blood triglyceride levels after taking oolong tea [Nihon Rinsho Eiyou Gakkai-shi (The Japanese Society of Clinical Nutrition Magazine) 1998; 20(1): 83-90]. These reports show that although drinking a large quantity of oolong tea is recognized to be effective, it is difficult in daily life to continue drinking such large quantities of a drink such as oolong tea. Further, simply providing concentrated oolong tea is not an appropriate and a practical option, due to its strong bitterness and astringency and increased caffeine content.

On the other hand, tea-derived tannins have been reported to have antioxidant activity (Biosci. Biotechnol. Biochem. 2003; 67(2): 396-401), and plant-derived tannins, especially tellimagrandin, have been reported to have not only antioxidant activity (Phytochemistry 1993; 33(3): 557-561) but also antibacterial properties (Microbiol. Immunol. 2004; 48(1): 67-73), anticancer properties (Toxicology Letters 2004; 147 (2): 109-119); and to function as a cytokine release regulators (JP 2004-510688-A), etc.

Patent Documents
   1. JP Shou 60-11912-B
   2. JP Hei 8-259557-A
   3. JP Hei 3-228664-A
   4. JP Hei 3-219872-A
   5. JP Hei 7-61927-A 6. JP Hei 1-102022-A
7. JP Hei 9-40689-A
8. JP Hei 9-291039-A
9. JP 2004-510688-A Non Patent Documents 1. Summary of 1999 National Nutrition Survey in Japan by The Ministry of Health, Labor and Welfare
2. Rinsho Eiyo (Clinical nutrition) 2001; 98(5): 577-588
3. Rinsyo Hyouka (Clinical evaluation), 1985; 13(2):
4. Rinsyo Hyouka (Clinical evaluation), 1985; 13(2):
5. Lancet 1998; 352:67-172
6. J. Nutr. 1988; 128: 56-60
7. Nihon Eiyou Shokuryou Gakkai-shi (Journal of Japanese society of Nutrition and Food Science) 1999; 52(2): 71-77
8. Kenkou Eiyou Shokuhin Kenkyu (Health food and nutrition food Research) 2002; 5(3): 131-144
9. J. Am. Coll. Nutr. 2000; 19(6): 789-796
10. Clin. Chim. Acta. 2001; 11(2): 109-117
11. Nutrition 2003; vol. 19, (10), 876-879
12. J. Nutr. 2002; 132, 1819-1824
13. Int. J. Obes. 1999; 23 98-105
14. Nihon Eiyou Shokuryou Gakkai-shi (Journal of Japanese society of Nutrition and food science) 1991; 44(4): 251-259
15. Nihon Rinsho Eiyou Gakkai-shi (The Japanese Society of Clinical Nutrition Magazine) 1998; 20(1): 83-90
16. Biosci. Biotechnol. Biochem. 2003; 67(2): 396-401
17. Phytochemistry 1993; 33(3): 557-561
18. Microbiol. Immunol. 2004; 48(1): 67-73
19. Toxicology Letters 2004; 147(2): 109-119

DISCLOSURE OF THE INVENTION

Problem to be Solved by the Invention

The present invention focuses on various polyphenol components contained in plants and provides lipase inhibitory agents comprising at least one of gallotannin and ellagitannin components isolated from tealeaves and *Tellima grandiflora*.

The present invention also provides high preference foods and/or beverages, containing said lipase inhibitory agents, for reducing blood triglyceride levels and promoting health without raising a problem of flavor.

The present invention further provides a pharmaceutical composition containing the lipase inhibitory agent which will suppress the absorption of dietary lipids and suppress the rise of triglycerides in blood.

Means for Solving Problem

As means for solving the stated problems, the present inventors found components from tealeaves and *Tellima grandiflora* which have a strong inhibitory effect on pancreatic lipase, an enzyme essential for fat absorption, and evaluated the lipase inhibitory activity of various polyphenols present therein, and ascertained that compounds having multiple gallic acid groups in their molecules have strong lipase inhibitory activity.

More specifically, lipase inhibitory agents of the present invention comprise as an active ingredient at least one of the compounds represented by formula I below:

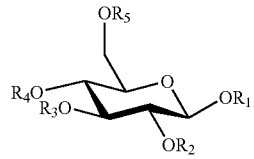

[formula 3]

wherein $R_1$, $R_2$ and $R_3$ independently represent H or a gallic acid residue, and $R_4$ and $R_5$ represent H or a gallic acid residue, or $R_4$ and $R_5$ together form an HHDP group represented by the formula below:

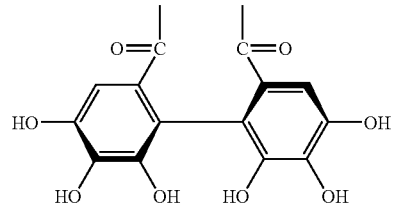

[formula 4]

provided that at least two of $R_1$ to $R_5$ represent a gallic acid residue or when all of $R_1$, $R_2$ and $R_3$ are H, $R_4$ and $R_5$ together form a HHDP group. As used herein, the gallic acid residue means the residue of gallic acid that has lost OH from its carboxyl group.

Preferred active ingredients are compounds of formula I wherein at least three of $R_1$ to $R_5$ are not H.

More preferred active ingredients are compounds of formula I wherein at least four of $R_1$ to $R_5$ are not H.

Still more preferred active ingredients are compounds of formula I wherein any of $R_1$ to $R_5$ are not H, e.g., compounds wherein all of $R_1$, $R_2$ and $R_3$ are gallic acid residue, and $R_4$ and $R_5$ together form the HHDP group (compound 8).

Examples of specific compounds contained in lipase inhibitory agents of the present invention include those shown in FIG. 1.

Lipase Inhibitory Agent

The lipase inhibitory compound of the present invention may be used as a lipase inhibitory agent either alone, or with a solvent or with a solid carrier. Preferably, the solvent or carrier is safe to use in foods or medicaments, considering its use in foods and/or beverages and/or medicamens mentioned below. The lipase inhibitory agent of the present invention can be used for various purposes, including, for example, experimental purposes, and as an active ingredient for preventing accumulation of triglycerides in foods and medicaments.

Method for Lipase Inhibitory Activity Determination

The lipase inhibitory agent of the present invention has strong inhibitory activity against lipase, particularly pancreatic lipase. This inhibitory activity can be determined by the method specifically described in Example 1.

Foods and/or Beverages Containing Lipase Inhibitory Agent

The lipase inhibitory agent of the invention may be added to foods and/or beverages in order to prevent an undesirable rise in blood triglycerides that may accompany fat intake in the diet, and/or to decrease increased blood triglyceride levels. Preferable examples of foods and/or beverages are those that are consumed daily, such as green tea, mugi-cha (barley tea), oolong tea, black tea, coffee, sports drinks, drinking water, seasonings and dressings. However, such foods and/or beverages may be any of those taken usually, such as soft drinks, cocktails, beer, whisky, shochu (rough distilled spirits), wine, sake, seasonings, dressings, flavored rice, processed food, instant food, retort pouch food (specially packaged food that has been pre-heated and sterilized), chocolate, fresh cream, confectionery, dairy products (nyu-seihin), health foods, and supplements.

The lipase inhibitory agent of the present invention is added to foods and/or to beverages to provide 0.1 mg to 10 g of active ingredient intake per meal. Provided that the lipase inhibitory agent of the present invention is derived from food, it is highly safe, and there is no practical upper limit to an amount which may be added to foods and/or to beverages.

A Pharmaceutical Drug Containing Lipase Inhibitory Agent

The lipase inhibitory agent of the present invention can also be used as an active ingredient in a drug for suppressing absorption of dietary lipids and preventing and/or decreasing an undesirable increase in blood triglyceride levels. Preferable drugs are those suitable for oral administration, such as drinks, tablets, capsules, granules, powders, candies and drops. Such drugs comprise the lipase inhibitory agent of the present invention in amounts of 0.1 mg to 10 g per dose.

Since the lipase inhibitory ingredient is highly safe, the pharmaceutical drug of the present invention can be administered over a long period of time without any risk of side effects. Therefore, it may be taken daily for the purpose of preventing or treating obesity as a life-style disease.

Effect of the Invention

By adding a lipase inhibitory agent containing at least one of gallotannin and ellagitannin components derived from tealeaves and *Tellima grandiflora*, the present invention provides high preference foods and/or beverages for reducing triglyceride levels and for promoting health, without raising a problem of flavor. In order to inhibit absorption of dietary lipids, it is desirable to take the lipase inhibitory agent with a meal. Therefore, beverages enriched with an active ingredient obtained from tea are of significant use. Especially, enrichment of beverages with these components enables the provision of beverages having anti-obesity effects and which promote health.

BRIEF EXPLANATION OF THE DRAWING

FIG. 1 shows the chemical structural formulae of the compounds evaluated for lipase inhibitory activity in Example 5.

EXAMPLES

Example 1

Lipase Inhibitory Activity Measurement

Lipase activity measurement was carried out by using oleic acid ester of fluorescence 4-methylumbelliferone (4-UMO) as a substrate, and measuring the fluorescence of 4-methylumbelliferone produced by reaction.

In the measurement, 13 mM Tris-HCl containing 150 mM NaCl and 1.36 mM $CaCl_2$ was used as a buffer (pH 8.0). Substrate 4-UMO (Sigma) is prepared as 0.1 M solution in DMSO and diluted 1000 times with the buffer mentioned above. Similarly, lipase (porcine pancreatic lipase (Sigma)) is prepared as 400 U/ml solution in the buffer mentioned above and used in enzymatic measurement.

50 µl of 4-UMO buffer solution and 25 µl of distilled water (or sample solution) are placed in 96 well microplate and mixed at 25 degrees, followed by adding 25 µl of lipase buffer solution to start enzyme reaction. After 30 minutes of reaction, 100 µl of 0.1 M citric acid buffer (pH 4.2) was added to terminate the reaction, and fluorescence of 4-methylumbelliferone (excitation wavelength: 355 nm, fluorescence wavelength: 460 nm) produced by the reaction was measured with a fluorescence plate reader (Labsystems, Fluoroskan Asent CF).

Inhibitory activity of the sample was determined as a sample amount which gives 50% of inhibition compared to the activity of control (distilled water.) ($IC_{50}$)(µM).

Test Samples

Gallic acid (compound 1) was purchased from Nacalai Tesque Inc. Compounds 2, 3, 4 and 5 were purified from oolong tea by the method described in the article published by Hashimoto et al. (Chem. Pharm. Bull. 1989; 37(12): 3255-3563, Chem. Pharm. Bull. 1989; 37(1): 77-85) (Example 2). 1,2,4,6-Tetragalloylglucose (compound 6) was purified from Camellia ptilophylla by the method of Example 3. Tellimagrandins (compounds 7, 8) were purified from *Tellima grandiflora* by the method of Example 4.

Example 2

Purifications of Gallotannins 2, 3, 4 and 5

Compounds 2, 3 and 5 were purified by the method described in the article published by Hashimoto et al. (Chem. Pharm. Bull. 1989; 37(12), 3255-3563). Briefly, oolong tea leaves were extracted with 80% acetone, after which the acetone was removed. The extract was then fractionated with water, methanol and 50% acetone on Sephadex LH-20 (Pharmacia). The fraction eluted with water-methanol was eluted with water-methanol on MCI-gel CHP-20P (Mitsubishi Kasei Corp.), and the resulting fraction was applied to Sephadex LH-20 (Pharmacia) again and eluted with water to give compounds 2 and 3. The fraction eluted with water-methanol was eluted with water-methanol on Sephadex LH-20 (Pharmacia) and then eluted with water-methanol on Fuji gel ODS-G3 (Fuji Silysia Chemical Ltd.) to give compound 5.

Compound 4 was purified by the method described in the article Chem. Pharm. Bull. 1989; 37(1): 77-85 as follows. Oolong tea leaves were extracted with 80% acetone, after which acetone was removed. The extract was then fractionated with water, methanol and 50% acetone on Sephadex LH-20 (Pharmacia). The methanol eluate was eluted with water-methanol on MCI-gel CHP-20P (Mitsubishi Kasei Corp.), and then eluted with water-methanol on Bondapak C18 (Waters) and further eluted with ethanol on Sephadex LH-20 (Pharmacia) to give compound 4.

Example 3

Purification of 1,2,4,6-tetragalloylglucose (Compound 6)

Dried leaves of Camellia ptilophylla (100 g) were extracted with 2000 ml of hot water (90° C.) for 4 min and lyophilized, and the resulting material was purified as follows. 1% aqueous solution of the lyophilized powder was adsorbed to Sep-Pak C18 Cartridge (5 ml, Waters) and washed with water. The fraction eluted with acetonitrile was then lyophilized. This fraction (250 mg) was applied onto Develosil C30-UG-5 (20 mm×250 mm, Nomura Chemical Co., Ltd.) and fractionated by elution with acetonitrile (linear gradient: 5 to 30%, 0.05% TFA, 5 ml/min, 180 min) while monitoring the absorbance at A280 nm. The fraction obtained was then applied onto YMC-Pak ODS (20×250 mm, YMC Co., Ltd.) and purified by elution with acetonitrile (linear gradient: 20 to 25%, 0.1% TFA, 6 ml/min, 60 min) to give 1,2,4,6-tetragalloylglucose (compound 6).

Example 4

Purifications of Tellimagrandins

Extraction and purification were performed according to Phytochemistry 1976; 15: 211-214 as follows. Leaves of *Tellima grandiflora* (100 g) were ground in liquid nitrogen and extracted with 1000 ml of 50% ethanol. The solvent was distilled off and then the residue was applied onto HP-20 (Mitsubishi Kasei Corp.) and washed with water. The fraction eluted with acetonitrile was then lyophilized. This fraction was applied onto Develosil ODS-UG-5 (50 mm×500 mm, Nomura Chemical Co., Ltd.) and fractionated by elution with acetonitrile (linear gradient: 5 to 25%, 0.05% TFA, 32 ml/min, 80 min) while monitoring the absorbance at A260 nm to give Tellimagrandin 1 and Tellimagrandin 2.

Example 5

Lipase Inhibitory Activity

Lipase inhibitory activities of gallocatechins and tellimagrandins (ellagitannins) derived from teas are shown in Table 1. To evaluate structure-activity correlation, $IC_{50}$ values are expressed in µM. Chemical structural formulae of the compounds subjected to evaluation are shown in FIG. 1.

Among these tannins, compounds having three or more molecules of gallic acid attached to the sugars (compounds 4, 6) and ellagitannins with HHDP group attached (compounds 5, 7, 8) showed lipase inhibitory activity. Gallic acid and glycosides having only one molecule of gallic acid showed no activity. Lipase inhibitory activity increases as the number of gallic acid molecule increases, demonstrating that the presence of at least two gallate groups in the molecule is required for expressing activity.

TABLE 1

| compound | IC50 (µM) |
| --- | --- |
| Galli acid (1) | >50 |
| β-glucogallin (2) | >50 |
| theogallin (3) | >50 |
| 1,4,6-tri-O-galloyl-D-glucose (4) | 1.226 |
| strictinin (5) | 0.472 |
| 1,2,4,6-tetra-GA-Glc (6) | 0.203 |
| Tellimagrandin1 (7) | 0.127 |
| Tellimagrandin2 (8) | 0.074 |

The invention claimed is:

1. A method for suppressing absorption of dietary lipids and/or suppressing a rise of triglycerides in blood in a mammal, wherein the method comprises administering to the mammal a composition containing at least one of compounds represented by formula I below:

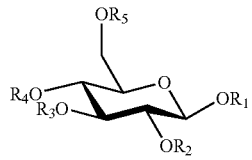

wherein $R_1$, $R_2$ and $R_3$ independently represent H or a gallic acid residue, and $R_4$ and $R_5$ represent H or a gallic acid residue, or $R_4$ and $R_5$ together form an HHDP group represented by the formula below:

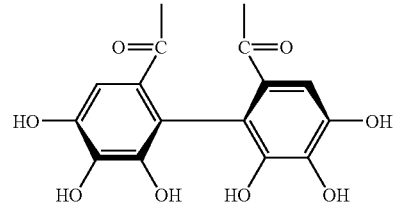

provided that at least two of $R_1$ to $R_5$ represent a gallic acid residue or when all of $R_1$, $R_2$ and $R_3$ are H, $R_4$ and $R_5$ together form the HHDP group, wherein the compound(s) are capable of suppressing absorption of dietary lipids and/or suppressing a rise of triglycerides in blood in the mammal.

2. The method of claim 1, wherein at least three of $R_1$ to $R_5$ are not H.

3. The method of claim 1, wherein at least four of $R_1$ to $R_5$ are not H.

4. The method of claim 1, wherein any of $R_1$ to $R_5$ are not H.

5. The method of claim 1, wherein all of $R_1$, $R_2$ and $R_3$ are a gallic acid residue, and $R_4$ and $R_5$ together form the HHDP group.

6. The method of claim 1, wherein the composition is a food or beverage, or a pharmaceutical composition.

7. The method of claim 1, wherein the composition contains at least one of the compounds in an amount of 0.1 mg or more per meal or 0.1 mg or more per dose.

8. The method of claim 7, wherein the composition contains at least one of the compounds in an amount of 0.1 mg to 10 g per meal or 0.1 mg to 10 g per dose.

9. The method of claim 6, wherein the composition is a food or beverage selected from the group consisting of tea drinks, soft drinks and health foods.

10. A method for inhibiting lipase activity in a mammal comprising administering to the mammal at least one of compounds represented by formula I below:

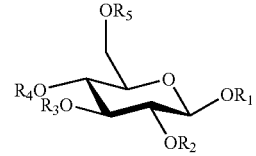

wherein $R_1$, $R_2$ and $R_3$ independently represent H or a gallic acid residue, and $R_4$ and $R_5$ represent H or a gallic acid residue, or $R_4$ and $R_5$ together form an HHDP group represented by the formula below:

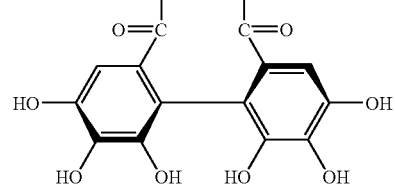

provided that at least two of $R_1$ to $R_5$ represent a gallic acid residue or when all of $R_1$, $R_2$ and $R_3$ are H, $R_4$ and $R_5$ together form the HHDP group, wherein the compound(s) are capable of inhibiting lipase activity in the mammal.

11. The method of claim 10, wherein at least three of $R_1$ to $R_5$ are not H.

12. The method of claim 10, wherein at least four of $R_1$ to $R_5$ are not H.

13. The method of claim 10, wherein any of $R_1$ to $R_5$ are not H.

14. The method of claim 10, wherein all of $R_1$, $R_2$ and $R_3$ are a gallic acid residue, and $R_4$ and $R_5$ together form the HHDP group.

15. A method for treating a disease or condition ameliorated by administering a lipase inhibitory agent in a mammal, wherein the method comprises administering to the mammal a composition containing at least one of compounds represented by formula I below:

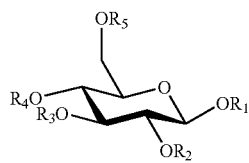

wherein $R_1$, $R_2$ and $R_3$ independently represent H or a gallic acid residue, and $R_4$ and $R_5$ represent H or a gallic acid residue, or $R_4$ and $R_5$ together form an HHDP group represented by the formula below:

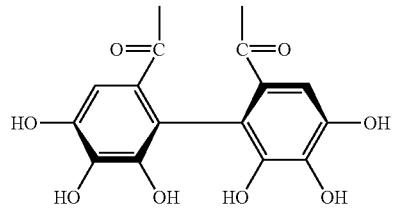

provided that at least two of $R_1$ to $R_5$ represent a gallic acid residue or when all of $R_1$, $R_2$ and $R_3$ are H, $R_4$ and $R_5$ together form the HHDP group, wherein the compound(s) are capable of treating the disease or condition ameliorated by administering a lipase inhibitory agent.

16. The method of claim 15, wherein the disease or condition is one selected form the group consisting of obesity, diabetes, hyperlipidemia, hypertension, arteriosclerosis and hipertriglyceridemia.

* * * * *